(12) United States Patent
Haley et al.

(10) Patent No.: US 7,893,278 B2
(45) Date of Patent: **\*Feb. 22, 2011**

(54) CIS-IMIDAZOLINES

(75) Inventors: Gregory Jay Haley, San Diego, CA (US); Norman Kong, West Caldwell, NJ (US); Emily Aijun Liu, Burlingame, CA (US); Binh Thanh Vu, North Caldwell, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/143,161

(22) Filed: Jun. 2, 2005

(65) Prior Publication Data

US 2005/0282803 A1  Dec. 22, 2005

Related U.S. Application Data

(60) Provisional application No. 60/580,441, filed on Jun. 17, 2004, provisional application No. 60/674,196, filed on Apr. 22, 2005.

(51) Int. Cl.
*A61K 31/4178* (2006.01)
*C07D 233/22* (2006.01)
*C07D 401/06* (2006.01)

(52) U.S. Cl. ............ 548/334.1; 514/396; 514/397

(58) Field of Classification Search ............ 548/334.1
See application file for complete search history.

(56) References Cited

U.S. PATENT DOCUMENTS

| 5,457,224 | A | 10/1995 | Ehrmann et al. |
| 6,617,346 | B1 | 9/2003 | Kong et al. |
| 6,734,302 | B2 | 5/2004 | Kong et al. |

FOREIGN PATENT DOCUMENTS

| EP | 363 061 | 4/1990 |
| EP | 1753727 | 2/2007 |
| WO | WO 00/78725 | 12/2000 |
| WO | 03/002509 | 1/2003 |
| WO | WO 03/051359 | * 6/2003 |
| WO | 2005/110996 | 11/2005 |

OTHER PUBLICATIONS

Golub et al., Science, vol. 286, Oct. 15, 1999, pp. 531-537.*
Hunter et al., Can. J. Chem., 50, pp. 669-677 (1972).
Vogtle et al., Chem. Ber., 109, pp. 1-40 (1976).
Wells et al., J. Org. Chem., 37, pp. 2158-2161 (1972).
Vassilev et al., Science, 303, pp. 844-848 (Feb. 6, 2004).
Jennerwein et al., J. Cancer Res. Clin. Oncol., 114, pp. 347-358 (1988).
McCapra et al., Photochem. and Photobiol., 4, pp. 1111-1121 (1965).
Carvajal et al, Cancer Research, vol. 65:5 pp. 1918-1924 (2005).
Japanese Office Action with translation for JP 2007-515829 dated Jul. 20, 2010.

* cited by examiner

*Primary Examiner*—Laura L. Stockton
(74) *Attorney, Agent, or Firm*—George W. Johnston; Patricia S. Rocha-Tramaloni

(57) ABSTRACT

The present invention relates to compounds of the formula

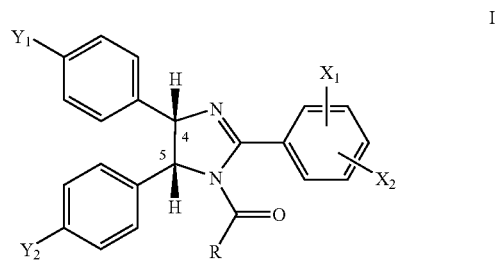

and the pharmaceutically acceptable salts and esters thereof, a process for their manufacture, medicaments containing them as well as the use of these compounds as pharmaceutically active agents. The compounds show antiproliferative activity and may be especially useful for the treatment of cancer.

7 Claims, No Drawings

CIS-IMIDAZOLINES

PRIORITY TO RELATED APPLICATIONS

This application claims the benefit of Provisional Application(s) Ser. No. 60/580,441, filed Jun. 17, 2004 and Ser. No. 60/674,196, filed Apr. 22, 2005.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

Wells et al. *J. Org. Chem.*, 1972, 37, 2158-2161, report synthesis of imidazolines. Hunter et al., *Can. J. Chem.*, 1972, Vol. 50, pgs. 669-77, report the preparation of amarine and isoamarine compounds which had previously been studied for chemiluminescence (McCapra et al. *Photochem. and Photobiol.* 1965, 4, 1111-1121). Zupanc et al. *Bull. Soc. Chem. & Tech.* (Yugoslavia) 1980-81, 27/28, 71-80, report the use of triaryl imidazolines as starting materials in the preparation of EDTA derivatives.

EP 363 061 to Matsumoto reports imidazoline derivatives useful as immunomodulators. The compounds were indicated to have low toxicity. Treatment and/or prevention of rheumatoid arthritis, multiple sclerosis, systemic lupus, erythemathodes, and rheumatic fever were implicated. WO 00/78725 to Choueiry et al. report a method for making substituted amidine compounds, and indicate that imidazoline-type compounds may be useful in the treatment of diabetes or related diseases involving impaired glucose disposal.

U.S. Pat. No. 6,617,346 B1 issued Sep. 9, 2003 and U.S. Pat. No. 6,734,302 B2 issued May 11, 2004 disclose related racemic cis-imidazolines. U.S. Pat. No. 6,734,302 B2 particularly discloses a closely related broad genus of racemic compounds which generally encompasses the presently claimed compounds save for the chirality and narrow genus of the present compounds.

SUMMARY OF THE INVENTION

The present invention provides at least one compound of formula I

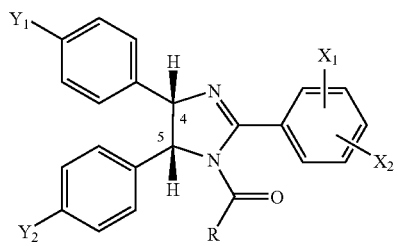

wherein X1, X2, Y1, Y$_2$, and R are as described herewithin as well as the pharmaceutically acceptable salts and esters thereof.

DETAILED DESCRIPTION OF THE INVENTION

The present invention provides chiral cis-imidazolines which are small molecule inhibitors of the MDM2-p53 interaction. In cell-free and cell-based assays, compounds of the present invention are shown to inhibit the interaction of MDM2 protein with a p53-like peptide with a potency that is approximately 100 fold greater than a p53-derived peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

The present invention provides at least one compound selected from a compound of formula I:

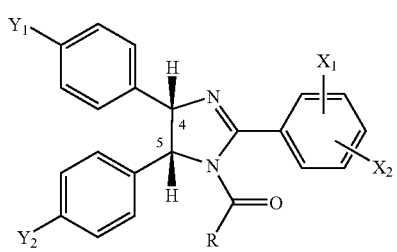

and the pharmaceutically acceptable salts and esters thereof, wherein

R is selected from saturated and unsaturated 5- and 6-membered rings containing at least one hetero atom wherein the hetero atom is selected from S, N and O and being optionally substituted with a group selected from lower alkyl, cycloalkyl, C=O—R$_1$, hydroxy, lower alkyl substituted with hydroxy, lower alkyl substituted with lower alkoxy, lower alkyl substituted with —NH$_2$, lower alkyl substituted with —C=O—R$_1$, N-lower alkyl, —SO$_2$CH$_3$, =O and —CH$_2$C=OCH$_3$, R$_1$ is selected from hydrogen, lower alkyl, —NH$_2$, —N-lower alkyl, lower alkyl substituted with hydroxy, lower alkyl substituted with NH$_2$, or a 5- or 6-membered saturated ring containing at least one hetero atom selected from S, N and O, X$_1$ and X$_2$ are independently selected from the group consisting of hydrogen, lower alkoxy, —CH$_2$OCH$_3$, —CH$_2$OCH$_2$CH$_3$, —OCH$_2$CF$_3$, —OCH$_2$CH$_2$F, Y$_1$ and Y$_2$ are each independently selected from the group consisting of —Cl, —Br, —NO$_2$, —C≡N, and —C≡CH, and the absolute stereochemistry at the 4 and 5 position of the imidazoline ring are S and R (as drawn in the formula I), respectively.

Preferred compounds are compounds of formula I wherein Y$_1$ and Y$_2$ are each independently selected from —Cl and —Br.

Further preferred compounds are compounds of formula I wherein R is piperazinyl substituted with at least one group selected lower alkyl, cycloalkyl, C=OR$_1$, lower alkyl substituted with hydroxy, lower alkyl substituted with —NH$_2$, lower alkyl substituted with —C=OR$_1$, N-lower alkyl, —SO$_2$CH$_3$, =O, —CH$_2$C=OCH$_3$, or piperidinyl substituted with at least one group selected from C1-C3 alkyl, —C1-C2 alkoxy, —C=OCH$_3$, —SO$_2$CH$_3$, —C=O, —OH, —CH$_2$NH$_2$, —C=OCH$_2$NH$_2$, —C=OCH$_2$OH, —C=OCH(OH)CH$_2$OH, —CH$_2$CH(OH)CH$_2$OH, —C=ON(CH$_2$)$_2$, —C=ONH$_2$, and —C=ON(CH$_3$)CH$_3$, —N(CH$_3$)CH$_3$, pyrrolidinyl and piperadinyl.

Also preferred are compounds of formula I wherein the X$_1$ group at ortho position is selected from lower alkoxy, —OCH$_2$CF$_3$ and —OCH$_2$CH$_2$F, and the X$_2$ group at para position is lower alkoxy.

Yet further preferred are compounds wherein the X$_1$ group at ortho position is selected from ethoxy, isopropoxy, —OCH$_2$CF$_3$ and —OCH$_2$CH$_2$F, and the X$_2$ group at para position is selected from methoxy and ethoxy.

Further preferred are compounds of formula I wherein R is selected from piperazinyl and substituted piperazinyl.

Such compounds are for example:

1-{4-[(4S,5R)-4,5-Bis-(4-chloro-phenyl)-2-(2-isopropoxy-4-methoxy-phenyl)-4,5-dihydro-imidazole-1-carbonyl]-piperazin-1-yl}-ethanone;

4-[(4S,5R)-4,5-Bis-(4-chloro-phenyl)-2-(2-isopropoxy-4-methoxy-phenyl)-4,5-dihydro-imidazole-1-carbonyl]-piperazin-2-one;

[(4S,5R)-4,5-Bis-(4-chloro-phenyl)-2-(2-isopropoxy-4-methoxy-phenyl)-4,5-dihydro-imidazol-1-yl]-(4-pyrrolidin-1-yl-piperidin-1-yl)-methanone;

4-[(4S,5R)-4,5-Bis-(4-chloro-phenyl)-2-(2-ethoxy-phenyl)-4,5-dihydro-imidazole-1-carbonyl]-piperazin-2-one;

1-{4-[(4S,5R)-4,5-Bis-(4-chloro-phenyl)-2-(2-ethoxy-phenyl)-4,5-dihydro-imidazole-1-carbonyl]-piperazin-1-yl}-ethanone;

2-{4-[(4S,5R)-4,5-Bis-(4-chloro-phenyl)-2-(2-ethoxy-phenyl)-4,5-dihydro-imidazole-1-carbonyl]-piperazin-1-yl}-1-morpholin-4-yl-ethanone;

[(4S,5R)-4,5-Bis-(4-chloro-phenyl)-2-(2-ethoxy-phenyl)-4,5-dihydro-imidazol-1-yl]-[4-(2-methanesulfonyl-ethyl)-piperazin-1-yl]-methanone; and

[(4S,5R)-4,5-Bis-(4-chloro-phenyl)-2-(2-isopropoxy-4-methoxy-phenyl)-4,5-dihydro-imidazol-1-yl]-(4-methyl-piperazin-1-yl)-methanone.

"Effective amount" means an amount that is effective to prevent, alleviate or ameliorate symptoms of disease or prolong the survival of the subject being treated.

"Halogen" means fluorine, chlorine, bromine or iodine.

"Hetero atom" means an atom selected from N, O and S.

"IC$_{50}$" refers to the concentration of a particular compound required to inhibit 50% of a specific measured activity. IC$_{50}$ can be measured, inter alia, as is described subsequently.

"Alkyl" denotes a straight-chained or branched saturated aliphatic hydrocarbon.

"Lower alkyl" groups denote C1-C6 alkyl groups and include methyl, ethyl, propyl, isopropyl, butyl, t-butyl, 2-butyl, pentyl, hexyl, and the like. Generally, lower alkyl is preferably C1-C4 alkyl, and more preferably C1-C3 alkyl.

"Cycloalkyl" means a non-aromatic, partially or completely saturated monovalent cyclic hydrocarbon radical containing 3 to 8 atoms. Examples of cycloalkyl groups include cyclopropyl, cyclobutyl, cyclopentyl and cyclohexyl.

"Alkoxy" denotes —O-alkyl. "Lower alkoxy" denotes —O-lower alkyl.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted" means that the substitution can occur at one or more positions and, unless otherwise indicated, that the substituents at each substitution site are independently selected from the specified options.

"Therapeutically effective amount" means an amount of at least one designated compound, that significantly inhibits proliferation and/or prevents differentiation of a human tumor cell, including human tumor cell lines.

Compounds of the present invention as exemplified advantageously show IC50s from about 0.020 uM to about 20 uM.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The present invention also provides pharmaceutical compositions comprising at least one compound of formula I, or a pharmaceutically acceptable salt or ester thereof, and a pharmaceutically acceptable carrier or excipient.

The compounds of the present invention can be prepared according to the following scheme 1.

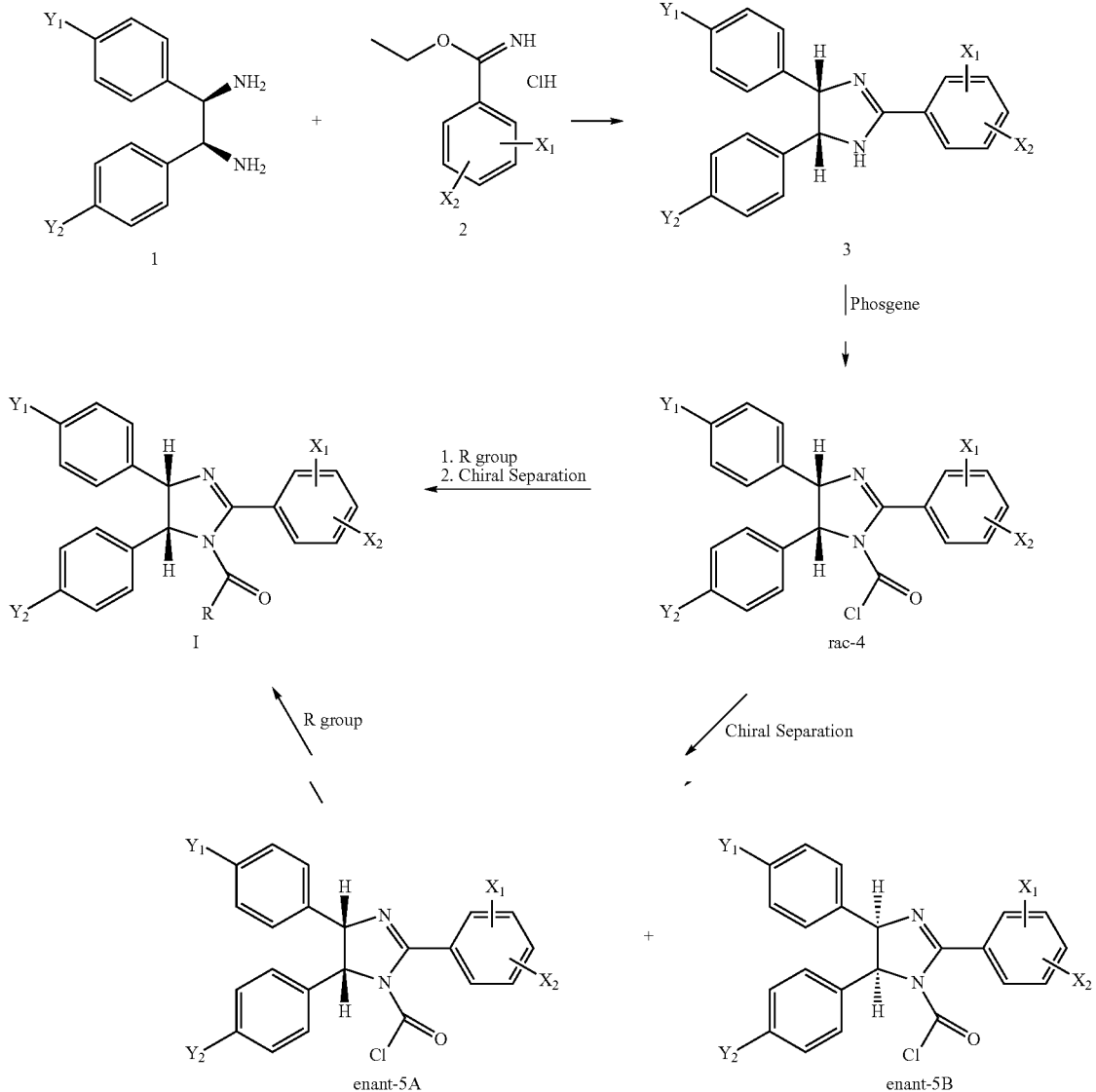

The synthesis commences with the coupling reaction of the benzimidate 2 (prepared from the corresponding benzonitriles using hydrogen chloride gas in ethanol, U.S. Pat. No. 6,617,346 B1) with meso-1,2-bis-(4-chlorophenyl)-ethane-1,2-diamine 1 (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40) in a solvent such as ethanol. Treatment of the imidazoline 3 with phosgene in the presence of a base such as triethylamine gives the racemic carbamoyl chloride 4. The enantiomers of the carbamoyl chloride rac-4 can be separated using chiral chromatography. The chiral stationary phase R,R-Whelk-O1, available through Regis Technologies, can be used. Coupling of the desired enantiomer 5A with appropriate amine groups (indicated as R group) provides the compounds of the formula I.

If it is desired, the racemic compounds of formula I can be prepared from rac-6 using appropriate amine groups (indicated as R group). The enantiomers of I then can be separated by chiral chromatography. The chiral stationary phase Diacel ChiralPak OD or AD can be used.

The absolute stereochemistry of the active enantiomer of I is determined based on the crystal structure of its complex with the human MDM2 (Vassilev et al. Science, 2004, 303, 844-848).

The following examples and references are provided to aid the understanding of the present invention, the true scope of which is set forth in the appended claims.

EXAMPLE 1

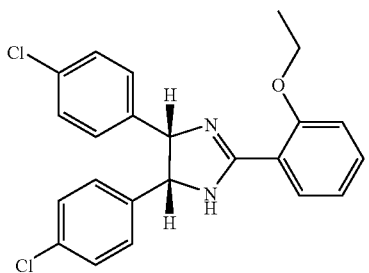

cis-4,5-Bis-(4-chloro-phenyl)-2-(2-ethoxy-phenyl)-4,5-dihydro-1H-imidazole was prepared according to the procedure as described in U.S. Pat. No. 6,617,346 B1.

EXAMPLE 2

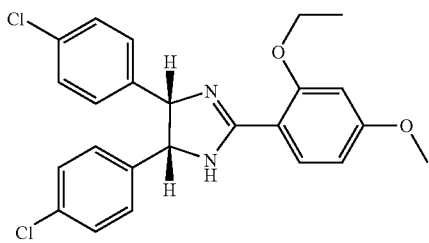

cis-4,5-Bis-(4-chloro-phenyl)-2-(2-isopropoxy-4-methoxy-phenyl)-4,5-dihydro-1H-imidazole was prepared according to the procedure as described in U.S. Pat. No. 6,617,346 B1.

EXAMPLE 3

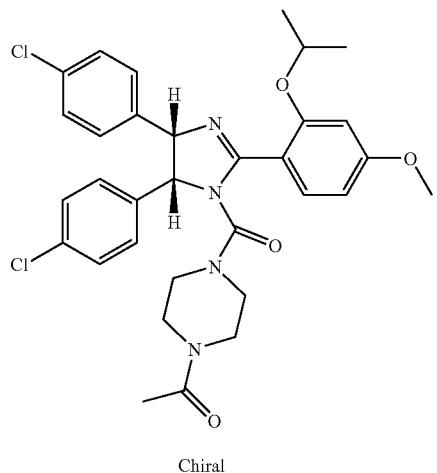

Chiral

1-{4-[(4S,5R)-4,5-Bis-(4-chloro-phenyl)-2-(2-isopropoxy-4-methoxy-phenyl)-4,5-dihydro-imidazole-1-carbonyl]-piperazin-1-yl}-ethanone To a solution of cis-4,5-bis-(4-chloro-phenyl)-2-(2-isopropoxy-4-methoxy-phenyl)-4,5-dihydro-1H-imidazole (5.48 g, 12.03 mmol, example 2) in methylene chloride (100 mL) cooled to 0° C. were sequentially added triethylamine (11.8 mL, 84.21 mmol) and phosgene (30.53 mL, 60.15 mmol, 21% solution in toluene). The reaction mixture was stirred at 0° C. under argon for 0.5 h or until thin layer chromatography (silica gel, 100% ethyl acetate) showed no starting material left. The solvent and excess reagents were removed under reduced pressure, and the residue was dried under vacuum for 1 h. The residue was dissolved in methylene chloride (100 mL) then a solution of 1-acetylpiperazine (1.619 g, 12.63 mmol) in methylene chloride (10 mL) was added. The reaction mixture was stirred for 1 h at room temperature (or until no starting material was seen by thin layer chromatography). Saturated sodium bicarbonate solution (10 mL) was added. The product was extracted with methylene chloride (2×50 mL). The organic layers were washed with brine (1×20 mL), dried (anhydrous sodium sulfate) and concentrated in vacuo. Purification of the crude residue by flash chromatography (Biotage system, KP-Sil™ 32-63 μm, 60 Å silica gel) eluting with 100% ethyl acetate then with 5% methanol in ethyl acetate gave rac-1-{4-[4,5-bis-(4-chloro-phenyl)-2-(2-isopropoxy-4-methoxy-phenyl)-4,5-dihydro-imidazole-1-carbonyl]-piperazin-1-yl}-ethanone as an orange foam (~7.2 g). It was recrystallized with methylene chloride and ethyl ether (6.721 g, white solids). Additional amount of rac-1-{4-[4,5-bis-(4-chloro-phenyl)-2-(2-isopropoxy-4-methoxy-phenyl)-4,5-dihydro-imidazole-1-carbonyl]-piperazin-1-yl}-ethanone (201 mg, tan color) was recovered from the mother liquor after purification by flash chromatography (Biotage system, KP-Sil™ 32-63 μm, 60 Å silica gel) eluting with 100% ethyl acetate then 5% methanol in ethyl acetate. Total yield: 6.922 g (94%). HR-MS (ES, m/z) calculated for $C_{32}H_{35}N_4O_4Cl_2$ [(M+H)$^+$] 609.2030, observed 609.2045.

The enantiomers of rac-1-{4-[4,5-bis-(4-chloro-phenyl)-2-(2-isopropoxy-4-methoxy-phenyl)-4,5-dihydro-imidazole-1-carbonyl]-piperazin-1-yl}-ethanone were separated by chiral chromatography (Daicel ChiralPak OD, eluting with 1:1 ethanol and hexanes). The first peak coming off the column is the desired enantiomer, 1-{4-[(4S,5R)-4,5-bis-(4-chloro-phenyl)-2-(2-isopropoxy-4-methoxy-phenyl)-4,5-dihydro-imidazole-1-carbonyl]-piperazin-1-yl}-ethanone. LR-MS (APCI): 609.12 [(M+H)$^+$].

EXAMPLE 4

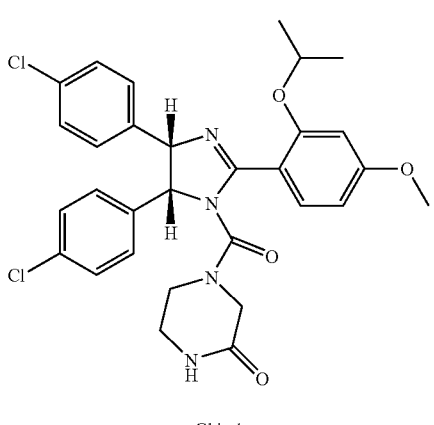

Chiral

4-[(4S,5R)-4,5-Bis-(4-chloro-phenyl)-2-(2-isopropoxy-4-methoxy-phenyl)-4,5-dihydro-imidazole-1-carbonyl]-piperazin-2-one was prepared from cis-4,5-bis-(4-chloro-phenyl)-2-(2-isopropoxy-4-methoxy-phenyl)-4,5-dihydro-1H-imidazole (example 2) and 2-piperazinone in an analogous manner as described in example 3. HR-MS (ES, m/z) calculated for $C_{30}H_{31}N_4O_4Cl_2$ [(M+H)$^+$] 581.1717, observed 581.1709.

EXAMPLE 5

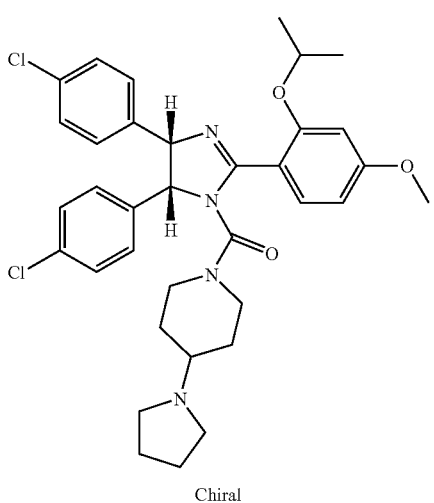

Chiral

[(4S,5R)-4,5-Bis-(4-chloro-phenyl)-2-(2-isopropoxy-4-methoxy-phenyl)-4,5-dihydro-imidazol-1-yl]-(4-pyrrolidin-1-yl-piperidin-1-yl)-methanone was prepared from cis-4,5-bis-(4-chloro-phenyl)-2-(2-isopropoxy-4-methoxy-phenyl)-4,5-dihydro-1H-imidazole (example 2) and 4-(1-pyrrolidinyl)piperidine in an analogous manner as described in example 3. HR-MS (ES, m/z) calculated for $C_{35}H_{41}N_4O_3Cl_2$ [(M+H)$^+$] 635.2550, observed 635.2558.

EXAMPLE 6

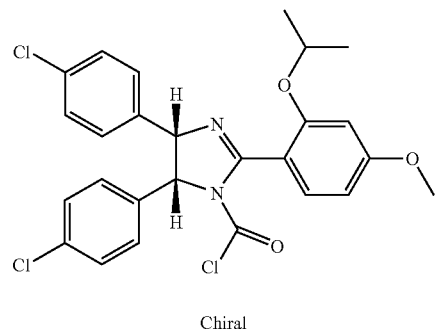

Chiral (4S,5R)-4,5-Bis-(4-chloro-phenyl)-2-(2-isopropoxy-4-methoxy-phenyl)-4,5-dihydro-imidazole-1-carbonyl chloride To a solution of cis-4,5-bis-(4-chloro-phenyl)-2-(2-isopropoxy-4-methoxy-phenyl)-4,5-dihydro-imidazole (5 g, 10.98 mmol, example 2) in methylene chloride (50 mL) cooled to 0° C. were added triethylamine (3 mL, 21.96 mL) and phosgene (8.7 mL, 16.47 mmol, ~20% solution in toluene), respectively. The reaction mixture was stirred at 0° C. for 30 min then the excess reagents and solvent were removed under reduced pressure. The residue was taken in methylene chloride (~100 mL) and the solution was filtered through a plug of silica gel (~50 g). The silica gel was washed with 20% ethyl acetate in hexanes. The filtrate was concentrated in vacuo and the residue was purified by flash chromatography (Biotage system, KP-Sil™ 32-63 µm, 60 Å silica gel, eluting with 5%, 10%, 20% ethyl acetate in hexanes) to give rac-4,5-bis-(4-chloro-phenyl)-2-(2-isopropoxy-4-methoxy-phenyl)-4,5-dihydro-imidazole-1-carbonyl chloride as white solids (4.31 g, 76%).

The enantiomers of rac-4,5-bis-(4-chloro-phenyl)-2-(2-isopropoxy-4-methoxy-phenyl)-4,5-dihydro-imidazole-1-carbonyl chloride were separated by chiral chromatography using a Waters Delta Prep 4000 and Modcol spring column (50 mm×70 cm) packed with R,R-Whelk-O1 spherical Kromasil silica gel (purchased from Regis Technologies). Eluent: 30% methylene chloride in hexane. Flowrate: 85 mL/min. Loading scale: ~2 g. The first peak coming off the column is the desired enantiomer, (4S,5R)-4,5-bis-(4-chloro-phenyl)-2-(2-isopropoxy-4-methoxy-phenyl)-4,5-dihydro-imidazole-1-carbonyl chloride.

EXAMPLE 7

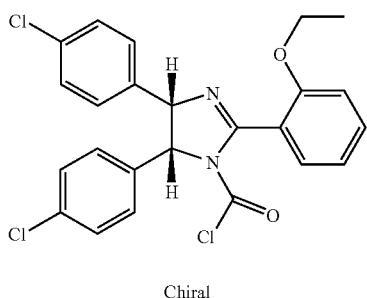

Chiral (4S,5R)-4,5-Bis-(4-chloro-phenyl)-2-(2-ethoxy-phenyl)-4,5-dihydro-imidazole-1-carbonyl chloride was prepared from 4,5-bis-(4-chloro-phenyl)-2-(2-ethoxy-phenyl)-4,5-dihydro-imidazole (example 1) and phosgene in an analogous manner as described in example 6.

EXAMPLE 8

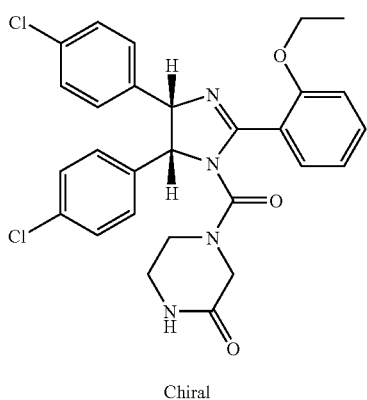

Chiral

4-[(4S,5R)-4,5-Bis-(4-chloro-phenyl)-2-(2-ethoxy-phenyl)-4,5-dihydro-imidazole-1-carbonyl]-piperazin-2-one To a solution of (4S,5R)-4,5-bis-(4-chloro-phenyl)-2-(2-ethoxy-phenyl)-4,5-dihydro-imidazole-1-carbonyl chloride (100 mg, 0.211 mmol, example 7) in methylene chloride (3 mL) cooled to 0° C. were added triethylamine (30 uL, 0.211 mmol) and 2-piperazinone (23 mg, 0.232 mmol), respectively. After 15 min, thin layer chromatography (silica gel, 20% ethyl acetate in hexanes) showed no starting material left. The reaction mixture was loaded into a flash silica gel column (12 g). Purification by flash column chromatography (eluting with 5% methanol and 0.1% triethylamine in ethyl acetate using Intelliflash 280 system) gave 4-[(4S,5R)-4,5-bis-(4-chloro-phenyl)-2-(2-ethoxy-phenyl)-4,5-dihydro-imidazole-1-carbonyl]-piperazin-2-one as a white foam (69 mg). HR-MS (ES, m/z) calculated for $C_{30}H_{31}N_4O_4Cl_2$ [(M+H)$^+$] 581.1717, observed 581.1717

EXAMPLE 9

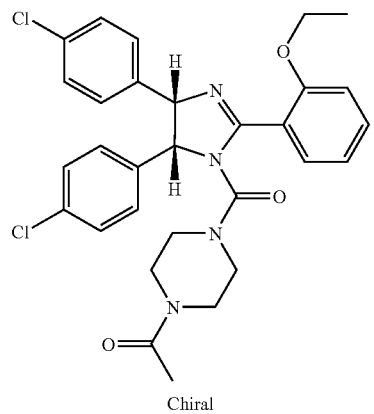

Chiral

1-{4-[(4S,5R)-4,5-Bis-(4-chloro-phenyl)-2-(2-ethoxy-phenyl)-4,5-dihydro-imidazole-1-carbonyl]-piperazin-1-yl}-ethanone was prepared from (4S,5R)-4,5-bis-(4-chloro-phenyl)-2-(2-ethoxy-phenyl)-4,5-dihydro-imidazole-1-carbonyl chloride (example 7) and 1-acetylpiperazine in an analogous manner as described in example 8. HR-MS (ES, m/z) calculated for $C_{30}H_{31}N_4O_3Cl_2$ [(M+H)$^+$] 565.1768, observed 565.1772.

EXAMPLE 10

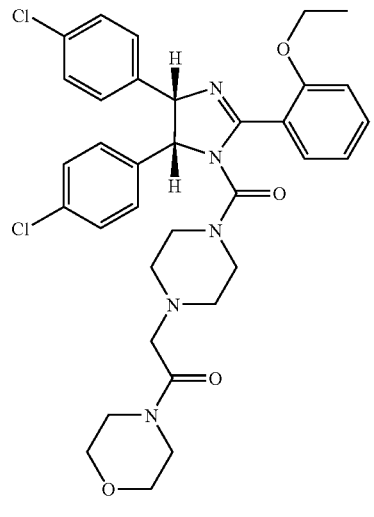

Chiral

2-{4-[(4S,5R)-4,5-Bis-(4-chloro-phenyl)-2-(2-ethoxy-phenyl)-4,5-dihydro-imidazole-1-carbonyl]-piperazin-1-yl}-1-morpholin-4-yl-ethanone was prepared from (4S,5R)-4,5-bis-(4-chloro-phenyl)-2-(2-ethoxy-phenyl)-4,5-dihydro-imidazole-1-carbonyl chloride (example 7) and 1-morpholin-4-yl-2-piperazin-1-yl-ethanone hydrochloride (Oakwood Chemicals) in an analogous manner as described in example 8. HR-MS (ES, m/z) calculated for $C_{34}H_{38}N_5O_4Cl_2$ [(M+H)$^+$] 650.2296, observed 650.2299.

EXAMPLE 11

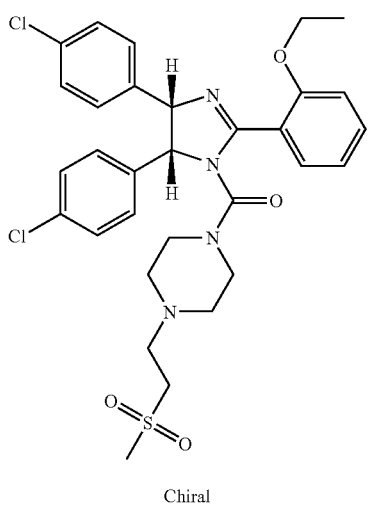

Chiral

[(4S,5R)-4,5-Bis-(4-chloro-phenyl)-2-(2-ethoxy-phenyl)-4,5-dihydro-imidazol-1-yl]-[4-(2-methanesulfonyl-ethyl)-piperazin-1-yl]-methanone Methyl vinyl sulfone (1.8 mL, 20.1 mmol) was added to a solution of 1-(tert-butyloxycarbonyl)piperazine (1.50 g, 8 mmol) in methanol (84 mL). The reaction mixture was stirred at room temperature for 4 h and concentrated to a white solid. Purification of the solid by flash column chromatography (silica gel, eluting with 1-5% methanol in methylene chloride) gave 1-tert-butyloxycarbonyl-4-(2-methanesulfonyl-ethyl)piperazine as a white solid (2.29 g, 95%).

Hydrochloric acid (42 mL, 168 mmol, 4 M in 1,4-dioxane) was added to a cooled solution of 1-tert-butyloxycarbonyl-4-(2-methanesulfonylethyl)piperazine (2.29 g, 7.8 mmol) in 1,4-dioxane (42 mL). The mixture was stirred at room temperature overnight then concentrated to give 1-(2-methanesulfonylethyl)piperazine bishydrochloride as a white solid (2.05 g).

(4S,5R)-4,5-Bis-(4-chloro-phenyl)-2-(2-ethoxy-phenyl)-4,5-dihydro-imidazole-1-carbonyl chloride (example 7) was reacted with 1-(2-methanesulfonylethyl)-piperazine bishydrochloride in methylene chloride using the procedure as described in example 8 to give [(4S,5R)-4,5-bis-(4-chloro-phenyl)-2-(2-ethoxy-phenyl)-4,5-dihydro-imidazol-1-yl]-[4-(2-methanesulfonyl-ethyl)-piperazin-1-yl]-methanone. HR-MS (ES, m/z) calculated for $C_{31}H_{35}N_4O_4SCl_2$ [(M+H)$^+$] 629.1751, observed 629.1757.

EXAMPLE 12

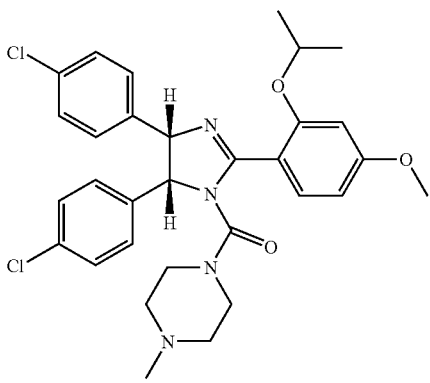

Chiral

[(4S,5R)-4,5-Bis-(4-chloro-phenyl)-2-(2-isopropoxy-4-methoxy-phenyl)-4,5-dihydro-imidazol-1-yl]-(4-methyl-piperazin-1-yl)-methanone was prepared from (4S,5R)-4,5-bis-(4-chloro-phenyl)-2-(2-isopropoxy-4-methoxy-phenyl)-4,5-dihydro-imidazole-1-carbonyl chloride (example 6) and 1-methylpiperazine in an analogous manner as described in example 8. HR-MS (ES, m/z) calculated for $C_{31}H_{35}N_4O_4SCl_2$ [(M+H)$^+$] 629.1751, observed 629.1757.

EXAMPLE 13

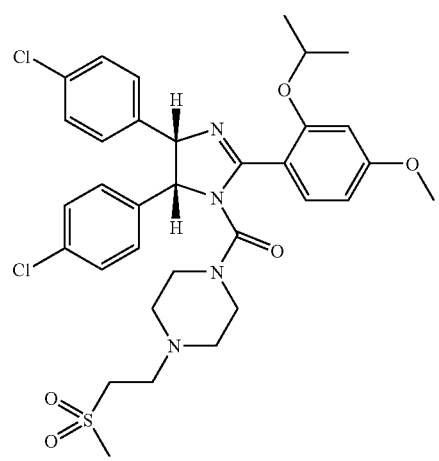

Chiral

[(4S,5R)-4,5-Bis-(4-chloro-phenyl)-2-(2-isopropoxy-4-methoxy-phenyl)-4,5-dihydro-imidazol-1-yl]-[4-(2-methanesulfonyl-ethyl)-piperazin-1-yl]-methanone was prepared from (4S,5R)-4,5-bis-(4-chloro-phenyl)-2-(2-isopropoxy-4-methoxy-phenyl)-4,5-dihydro-imidazole-1-carbonyl chloride (example 6) and 1-(2-methanesulfonylethyl)-piperazine (example 11) in an analogous manner as described in example 8. LR-MS: 673.3 [(M+H)$^+$].

EXAMPLE 14

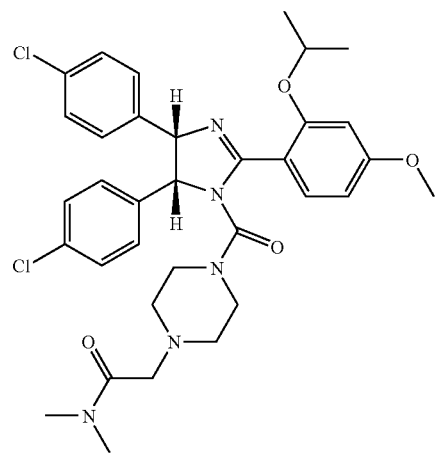

Chiral

2-{4-[(4S,5R)-4,5-Bis-(4-chloro-phenyl)-2-(2-isopropoxy-4-methoxy-phenyl)-4,5-dihydro-imidazole-1-carbonyl]-piperazin-1-yl}-N,N-dimethyl-acetamide was prepared from (4S,5R)-4,5-bis-(4-chloro-phenyl)-2-(2-isopropoxy-4-methoxy-phenyl)-4,5-dihydro-imidazole-1-carbonyl chloride (example 6) and N,N-dimethyl-2-piperazin-1-yl-acetamide (Oakwood Chemicals) in an analogous manner as described in example 8. LR-MS: 652.3 [(M+H)$^+$].

EXAMPLE 15

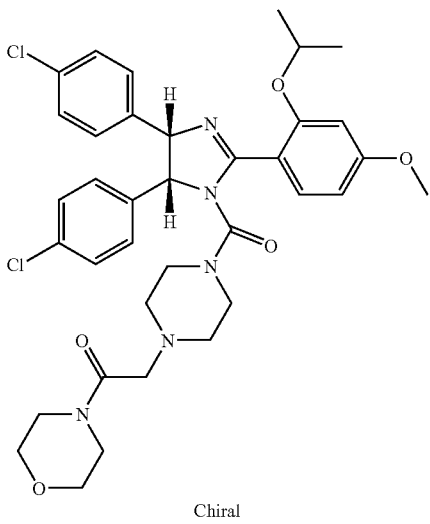

Chiral

2-{4-[(4S,5R)-4,5-Bis-(4-chloro-phenyl)-2-(2-isopropoxy-4-methoxy-phenyl)-4,5-dihydro-imidazole-1-carbonyl]-piperazin-1-yl}-1-morpholin-4-yl-ethanone was prepared from (4S,5R)-4,5-bis-(4-chloro-phenyl)-2-(2-isopropoxy-4-methoxy-phenyl)-4,5-dihydro-imidazole-1-carbonyl chloride (example 6) and 1-morpholin-4-yl-2-piperazin-1-yl-ethanone hydrochloride (Oakwood Chemicals) in an analogous manner as described in example 8. LR-MS: 694.3 [(M+H)$^+$].

EXAMPLE 16

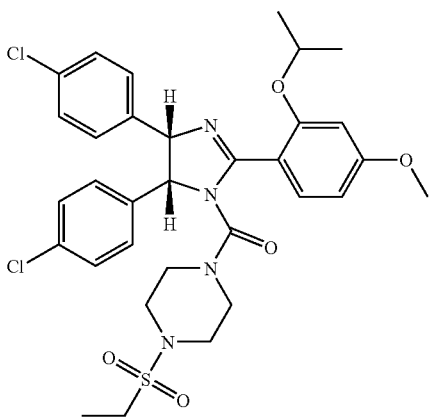

Chiral

[(4S,5R)-4,5-Bis-(4-chloro-phenyl)-2-(2-isopropoxy-4-methoxy-phenyl)-4,5-dihydro-imidazol-1-yl]-(4-ethanesulfonyl-piperazin-1-yl)-methanone was prepared from (4S,5R)-4,5-bis-(4-chloro-phenyl)-2-(2-isopropoxy-4-methoxy-phenyl)-4,5-dihydro-imidazole-1-carbonyl chloride (example 6) and 1-ethanesulfonyl-piperazine (prepared from 1-tert-butyloxycarbonyl-piperazine and ethanesulfonyl chloride) in an analogous manner as described in example 8. LR-MS: 659.2 [(M+H)$^+$].

EXAMPLE 17

In Vitro Activity Assay

The ability of the compounds to inhibit the interaction between p53 and MDM2 proteins was measured by an ELISA (Enzyme-Linked Immuno Sorbent Assay) in which recombinant GST-tagged MDM2 binds to a peptide that resembles the MDM2-interacting region of p53 (Böttger et al., J. Mol. Bio. 1997, Vol. 269, pgs. 744-756). This peptide is immobilized to the surface of a 96 well plate via N-terminal biotin which binds to streptavidin-coated wells. MDM2 is added to each well in the presence of anti-MDM2 mouse monoclonal antibody (SMP-14, Santa Cruz Biotech). After removal of the unbound MDM2 protein, a peroxydase-linked secondary antibody (anti-mouse IgG, Roche Molecular Biochemicals) and the amount of peptide-bound MDM2 is determined colorimetrically by the addition of a peroxydase substrate (MTB Microwell Peroxydase Substrate System, Kirkegaard & Perry Labs).

Test plates were prepared by coating with streptavidin (5 mg/ml in PBS) for 2 hours followed by a PBS (phosphate-buffered saline) wash and overnight blocking with 150 uL of blocking buffer containing 2 mg/ml bovine serum albumin (Sigma) and 0.05% Tween 20 (Sigma) in PBS at 4° C. Biotinylated peptide (1 uM) is added to each well in 50 uL of blocking buffer and washed extensively after 1 h incubation. Test compounds were diluted in a separate 96 well plate and added in triplicate to a compound incubation plate containing a mix of the MDM2 protein and anti-MDM2 antibody. After 20 min incubation, the content of the plate is transferred to the test plate and incubated for an additional 1 hour. The secondary anti-mouse IgG antibody is added to the test plate preceded and followed by a triple wash with 0.05% Tween 20 in PBS. Finally, peroxydase substrate is added to each well and the absorption was read using a plate reader (MR7000, Dynatech) at 450 nm. The inhibitory activity of the test compounds was measured as a percentage of the bound MDM2 in treated vs. untreated wells and IC$_{50}$ was calculated.

IC50s showing biological activity that applies to compounds of the subject matter of this invention ranges from about 0.020 uM to about 20 uM. Specific data for some examples are as follows:

| Example | IC50 (uM) |
|---------|-----------|
| 4 | 0.604 |
| 5 | 0.071 |

What is claimed is:

1. A compound of formula

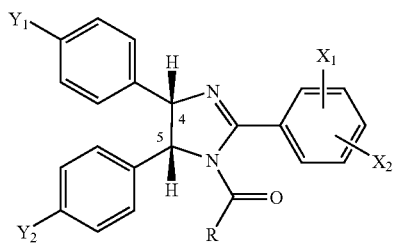

or the pharmaceutically acceptable salts thereof, wherein

R is selected from saturated and unsaturated 5- and 6-membered rings containing at least one hetero atom wherein the hetero atom is selected from S, N or O and said ring being substituted with a lower alkyl which alkyl is further substituted with at least one group selected from —C=O—$R_1$, —$SO_2CH_3$, or —$CH_2C$=$OCH_3$, $R_1$ is selected from the group consisting of hydrogen, —$NH_2$, —N-lower alkyl, lower alkyl substituted with hydroxy, lower alkyl substituted with $NH_2$, and a 5- or 6-membered saturated ring containing at least one hetero atom selected from S, N and O, $X_1$ and $X_2$ are independently selected from the group consisting of hydrogen, lower alkoxy, —$CH_2OCH_3$, —$CH_2OCH_2CH_3$, —$OCH_2CF_3$ and —$OCH_2CH_2F$, $Y_1$ and $Y_2$ are each independently selected from the group consisting of —Cl, —Br, —$NO_2$, —C≡N, and —C≡CH, and the absolute stereochemistry at the 4 and 5 position of the imidazoline ring are S and R respectively.

2. The compound of claim 1 wherein $Y_1$ and $Y_2$ are each independently selected from —Cl and —Br.

3. A compound of the formula

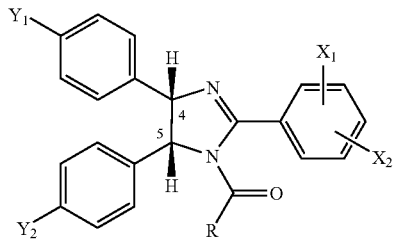

wherein R is piperazinyl substituted with lower alkyl which alkyl is further substituted with at least one group selected from —C=$OR_1$, —$SO_2CH_3$, or —$CH_2C$=$OCH_3$, wherein $R_1$ is selected from hydrogen, —$NH_2$, —N-lower alkyl, lower alkyl substituted with hydroxy, lower alkyl substituted with $NH_2$, $X_1$ and $X_2$ are independently selected from the group consisting of hydrogen, lower alkoxy; —$CH_2OCH_3$, —$CH_2OCH_2CH_3$, —$OCH_2CF_3$ and —$OCH_2CH_2F$, $Y_1$ and $Y_2$ are each independently selected from the group consisting of —Cl, —Br, —$NO_2$, —C≡N, and —C≡CH or the pharmaceutically acceptable salts thereof.

4. The compound of claim 3 wherein the $X_1$ group at ortho position is selected from lower alkoxy, —$OCH_2CF_3$ or —$OCH_2CH_2F$, and the $X_2$ group at para position is lower alkoxy.

5. The compound of claim 4 wherein the $X_1$ group at ortho position is selected from ethoxy, isopropoxy, —$OCH_2CF_3$ or —$OCH_2CH_2F$, and the $X_2$ group at para position is selected from methoxy or ethoxy.

6. A pharmaceutical composition comprising: a compound of the formula

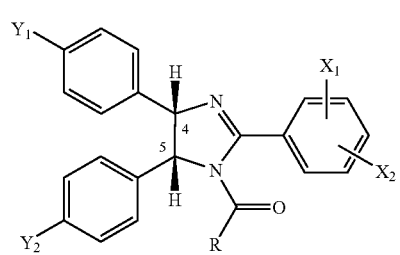

or the pharmaceutically acceptable salts thereof, wherein

R is selected from saturated and unsaturated 5- and 6-membered rings containing at least one hetero atom wherein the hetero atom is selected from S, N or O and said ring being substituted with lower alkyl which alkyl is further substituted with at least one group selected from —C=O—$R_1$, —$SO_2CH_3$, or —$CH_2C$=$OCH_3$, $R_1$ is selected from hydrogen, —$NH_2$, —NH-lower alkyl, lower alkyl substituted with hydroxy, lower alkyl substituted with $NH_2$, or a 5- or 6-membered saturated ring containing at least one hetero atom selected from S, N and O, $X_1$ and $X_2$ are independently selected from the group consisting of hydrogen, lower alkoxy, —$CH_2OCH_3$, —$CH_2OCH_2CH_3$, —$OCH_2CF_3$ and —$OCH_2CH_2F$, $Y_1$ and $Y_2$ are each independently selected from the group consisting of —Cl, —Br, —$NO_2$, —C≡N, and —C≡CH, and the absolute stereochemistry at the 4 and 5 position of the imidazoline ring are S and R respectively; and a pharmaceutically acceptable carrier or excipient.

7. A compound of the formula

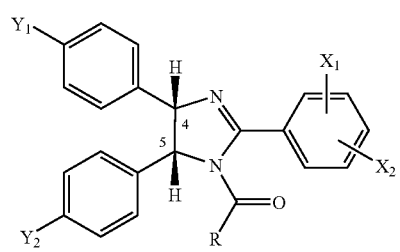

wherein R is
piperidinyl substituted with at least one group selected from the group consisting of $-SO_2CH_3$, $-C=OCH_2NH_2$, $-C=OCH(OH)CH_2OH$ and $-C=ON(CH_3)CH_3$, $X_1$ and $X_2$ are independently selected from the group consisting of hydrogen, lower alkoxy, $-CH_2OCH_3$, $-CH_2OCH_2CH_3$, $-OCH_2CF_3$ and $-OCH_2CH_2F$, $Y_1$ and $Y_2$ are each independently selected from the group consisting of $-Cl$, $-Br$, $-NO_2$, $-C\equiv N$, and $-C\equiv CH$ or the pharmaceutically acceptable salts thereof.

\* \* \* \* \*